United States Patent [19]
Fujita et al.

[11] Patent Number: 5,928,661
[45] Date of Patent: Jul. 27, 1999

[54] CONTROLLED RELEASE COMPOSITION CONTAINING VOLATILE COMPOUND

[75] Inventors: Masao Fujita; Shuji Hirohama; Yoshihiro Hayashi; Shinichi Igarashi, all of Sakai-gun; Yuichi Mizukami, Osaka; Yasushi Sekiyama, Osaka; Asami Takata, Osaka, all of Japan

[73] Assignees: Rengo Co., Ltd.; The Green Cross Corporation, both of Osaka, Japan

[21] Appl. No.: 08/864,990

[22] Filed: May 29, 1997

[30] Foreign Application Priority Data

May 31, 1996 [JP] Japan ................................. 8-139301

[51] Int. Cl.⁶ ..................................................... A01N 25/34
[52] U.S. Cl. ............................................ 424/402; 424/405
[58] Field of Search ..................................... 424/402, 405

[56] References Cited

U.S. PATENT DOCUMENTS

| | | | |
|---|---|---|---|
| 4,983,404 | 1/1991 | Raman et al. ........................ | 426/3 |
| 5,246,663 | 9/1993 | Ohama et al. ........................ | 422/30 |
| 5,417,974 | 5/1995 | Sekiyama et al. .................... | 424/411 |
| 5,436,268 | 7/1995 | Ohama et al. ........................ | 514/514 |
| 5,472,483 | 12/1995 | Kimura et al. ...................... | 106/18.34 |
| 5,695,779 | 12/1997 | Mori ..................................... | 424/448 |

*Primary Examiner*—Jose' G. Dees
*Assistant Examiner*—Kathryne E. Shelborne
*Attorney, Agent, or Firm*—Sughrue, Mion, Zinn, Macpeak & Seas, PLLC

[57] ABSTRACT

A controlled release composition comprising a volatile compound such as allyl isothiocyanate and a rosin in a proportion of 0.1 to 100 parts by weight of the compound per 100 parts by weight of the rosin, the controlled release composition further comprising a plasticizer, and the controlled release composition laminated on a substrate or in other forms. The AIT controlled release composition of the present invention can be used for emission of aroma, antimicrobial effect, antibacterial effect, insecticidal action, insectproof effect, fungicidal action, fungiproof action, freshness retention, antiseptic or preservative effect and the like.

12 Claims, 7 Drawing Sheets

5,928,661

CONTROLLED RELEASE COMPOSITION CONTAINING VOLATILE COMPOUND

TECHNICAL FIELD OF THE INVENTION

The present invention relates to a controlled release composition aiming at a controlled release of a volatile compound. More particularly, the present invention relates to a controlled release composition suitable for releasing, in a controlled manner, a volatile compound contained therein, in a limited space or indoors or in an open space.

BACKGROUND OF THE INVENTION

A volatile compound such as aromatic and essential oil has been released in a controlled manner by mixing the volatile compound with an ethylene-vinyl acetate resin and the like, enclosing same in cyclodextrin, mixing same with a naturally occurring shellac resin, and other method.

However, the conventional methods are associated with problems in that, due to the high melting point of synthetic resin such as ethylene-vinyl acetate resin, a volatile compound is volatilized when being mixed with the synthetic resin to reduce its yield, and that the volatile compound considerably softens the produced composition as a result of its plasticizing effect, thereby decreasing sustained release by the synthetic resin. While cyclodextrin may be used, cyclodextrin itself is costly, and does not permit easy control of release rate, since the volatile compound is not released unless placed in a certain range of humidity, whereas rapidly released in too high a humidity.

In the meantime, a naturally occurring shellac resin is superior in safety and control of release rate, whereas the release property thereof changes rather easily according to humidity. When it is heat-melted to be mixed with a volatile compound, it tends to be thermoset to degrade workability during production or processability of the obtained mixed composition.

As the situation stands, there has been a great demand for a controlled release composition containing a volatile compound, which composition being superior in the controlled release of the volatile compound, particularly controlled release of the volatile compound in a limited space or indoors or in an open space, and free of problems of a varying release rate due to humidity and thermosetting during production process.

SUMMARY OF THE INVENTION

As a result of the study and investigation in an attempt to solve the above-mentioned problems, it has been found that rosin is capable of naturally releasing a volatile compound with ease from a mixture of the volatile compound and the rosin, even without any special physical means, that rosin allows release of said compound to the level unexpectedly superior, that it is chemically more stable when compared to shellac conventionally used, and that it is free of the above-mentioned problems of varying release rate due to humidity and thermosetting during production process. Further studies have revealed that a concurrent use of a plasticizer enables an easy production of a controlled release composition more stable in quality and having excellent processability, which resulted in the completion of the present invention.

Accordingly, the present invention provides the following.

1) A controlled release composition comprising a volatile compound and a rosin in a proportion of 0.1 to 100 parts by weight, particularly 0.2 to 30 parts by weight, of the compound per 100 parts by weight of the rosin.
2) The controlled release composition of 1) above, wherein the volatile compound is allyl isothiocyanate.
3) The controlled release composition of 1) or 2) above, further comprising a plasticizer particularly in a proportion of 1 to 25 parts by weight per 100 parts by weight of rosin.
4) The controlled release composition of 3) above, wherein the plasticizer is at least one kind selected from the group consisting of fatty acid, fatty acid ester, phosphoric ester and wax.
5) The controlled release composition of any one of the above 1) to 4), wherein the rosin and the volatile compound are contained in a proportion of at least 60% by weight in total.
6) The controlled release composition of any one of the above 1) to 5), which is in the form of a plate, block, powder, granule or tablet.
7) The controlled release composition of any one of the above 1) to 5), which is adhered to one or both sides of a film or sheet substrate.
8) The controlled release composition of any one of the above 1) to 5), which is sandwiched between two substrates, particularly the composition sandwiched between an unoriented polypropylene film and a polyester film.
9) The controlled release composition of any one of the above 1) to 5), which is entrapped in a fibrous substrate.

DETAILED DESCRIPTION OF THE INVENTION

Figure 1:
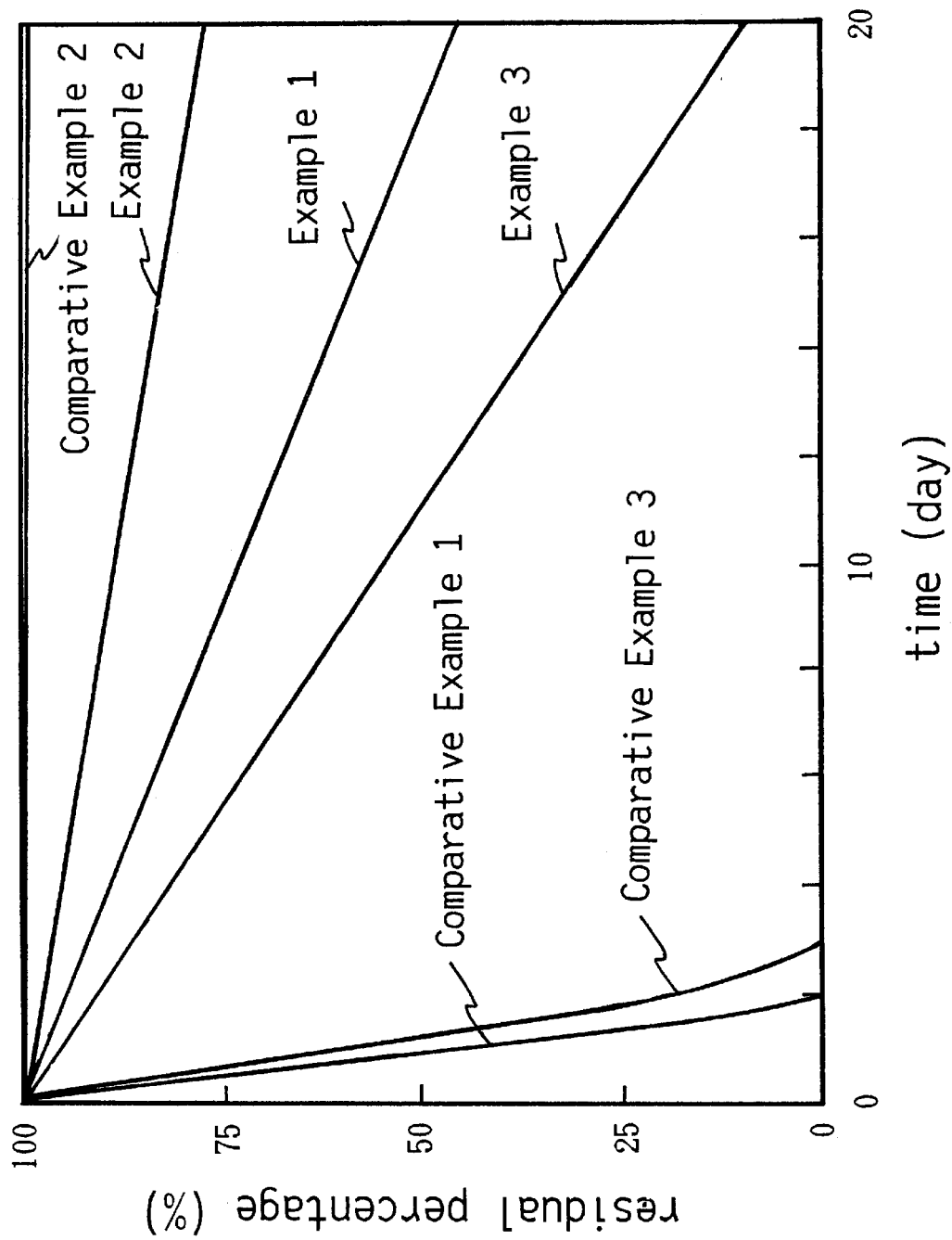
FIG. 1 is a graph showing the residual percentage of contained volatile compounds of Examples 1 to 3 and Comparative Examples 1 to 3 in relation to the time (days) during which the compounds were allowed to stand under isothermal and isohumidity conditions.

The rosin to be used in the present invention includes, for example, natural rosin including one or two kinds of organic acids such as abietic acids (e.g., abietic acid, neoabietic acid, dihydroabietic acid, tetrahydroabietic acid, dehydroabietic acid and the like) and pimaric acids (e.g., d-pimaric acid, iso-d-pimaric acid, levopimaric acid and the like); and those obtained by processing rosin produced in various countries in the world, such as rosin gum, tall oil rosin, wood rosin, denatured rosin obtained by subjecting the above-mentioned rosins to hydrogenation, disproportionation, polymerization and the like, and rosin esters (e.g., ester gum) obtained by esterification of the above-mentioned various rosins. These rosins are thermoplastic solids at ordinary temperature, and have a melting point of about 80° C. to about 130° C. Of these, those having a melting point of not more than 110° C., particularly those having a melting point of not more than 100° C., can advantageously lower the rosin melting temperature for the production of the composition of the present invention and lessen, to the greatest possible extent, vaporization and loss upon mixing the volatile compound to be mentioned later and rosin.

The volatile compound to be used in the present invention may be, for example, one or more kinds of various natural and synthetic compounds capable of exerting aromatic effect, odor extinguishing action, bacteriocidal action, antibacterial action, fungicidal action, fungiproof action, insecticidal action, insectproof action and other beneficial actions in the form of vapor, and volatile under the environment in which the composition of the present invention is used. Especially, a volatile compound is preferable which has an equilibrium vapor pressure of at least 0.001 mmHg, particularly not less than 0.003 mmHg, at an environment temperature at which the composition of the present invention is used, such as room temperature.

Examples of the volatile compound include natural and synthetic substances such as pinene, limonene, linalool, menthol, terpenol, eugenol, acetophenone, lavender oil, hinoki oil, eucalyptus oil, peppermint oil, spearmint oil, rose oil, mustard oil, hiba oil, hinokitiol, chlorine dioxide, thiocyanic acid compounds, isothiocyanic acid compounds, allyl isothiocyanate and the like.

When the content of the volatile compound is too small relative to that of rosin, it is difficult to substantially release the volatile compound. Conversely, however, when the content is excessively great, rosin shows poor control of release and some volatile compounds plasticize rosin to ultimately soften the obtained mixed composition to the extent that it cannot be molded into a desired product form. Hence, the content of the volatile compound is 0.1 to 100 parts by weight, preferably 0.2 to 30 parts by weight, more preferably 1 to 25 parts by weight, per 100 parts by weight of rosin.

The use of a plasticizer in the present invention facilitates mixing and kneading for the production of the composition of the present invention, which in turn results in less amounts of volatile compound volatilized during the production process, and reduction and prevention of poor dispersion, which is ascribed to the volatilization, of the volatile compound in the composition. The plasticizer may be any as long as such effects can be attained, and exemplified by fatty acid, fatty acid ester, phosphoric ester, wax and the like.

Examples of fatty acid include stearic acid and lauric acid. Fatty acid ester may be, for example, sorbitan laurate, dibutyl sebacate or the like. As phosphoric ester, usable are, for example, 2-ethylhexyldiphenyl phosphate and the like. Wax may be, for example, ester wax of a fatty acid such as a plant wax (e.g., carnauba wax and cotton wax) and an animal wax (e.g., beeswax and wool wax), and a higher monohydric or dihydric alcohols, montan wax, ozokerite, microcrystalline wax, petrolatum and the like.

A plasticizer used in too small an amount cannot provide any effect, whereas an excess thereof generally, though depending on the kind of the plasticizer, oversoftens the obtained composition, thus possibly making preparation into a desired product form difficult to achieve. Hence, the content of the plasticizer is 0.1 to 100 parts by weight, preferably 1 to 25 parts by weight, per 100 parts by weight of rosin. Particularly preferable composition ratio in the context of the present invention is 1 to 25 parts by weight of the volatile compound and 1 to 25 parts by weight of the plasticizer, both per 100 parts by weight of rosin.

The plasticizer includes those capable of improving mixing and kneading for the production of the composition of the present invention, as well as processability of the resulting composition and maintenance of the form of the obtained product. Examples of such plasticizer include the aforesaid various waxes which may be used in an amount greater than that of other plasticizers.

The controlled release composition of the present invention may contain various additives conventionally used, such as coloring agent, bonding preventive and the like, as long as they do not impair the object of the present invention. Note that when the total content of rosin and volatile compound in the controlled release composition of the present invention is small, various problems stemming from insufficient rosin content arise, such as propensity toward degraded control of release, poor form processability and poor maintenance of the form of the obtained product, as well as shorter time of volatilization due to the less volatile compound content and the like. Thus, the total content of the rosin and volatile compound in the controlled release composition of the present invention is preferably at least 60% by weight, particularly not less than 80% by weight.

The controlled release composition of the present invention can be produced by adding and mixing the volatile compound to and with rosin melted by heating, in the air or in an inert atmosphere (e.g., nitrogen gas and carbon dioxide) to prevent oxidative degradation of other components added, particularly rosin. When a plasticizer is used, it may be mixed in advance with rosin, or may be added to rosin together with the volatile compound.

The volatile compound to be used in the present invention may be liquid or solid at room temperature. A liquid may be added alone or added in a powdery form carried by a suitable carrier used conventionally and inert to the volatile compound, such as pulp, paper, cellulose particles, zeolite, alumina, silica gel and calcium silicate. When it is solid at room temperature, it can be added in a powdery form.

Inasmuch as the volatile compound is literally volatile in substance, it is industrially important to reduce, to the greatest possible extent, the amount vaporized and lost during production process of the composition of the present invention, particularly due to the high temperature used for mixing. For this end, it is preferable to lower the temperature at which the rosin is melted during production to, for example, not more than 100° C., preferably 75–90° C. In general terms, a means is preferably taken such as completing mixing efficiently in a short time, adopting an enclosed type mixer such as a Henschel mixer, cooling as necessary immediately after mixing, and form processing along with cooling into a desired form and packaging the resulting product to airtightly enclose same. When a plasticizer is used, a volatile compound mixed thoroughly in advance with a necessary amount of the plasticizer in an enclosed space may be advantageously added to the rosin.

The controlled release composition of the present invention can be used in various forms according to the object of use. For example, the controlled release composition of the present invention alone is formed into a plate, powder, tablet or block having a special shape.

In addition, the controlled release composition of the present invention can be used in combination with various substrates. Examples of such substrate include solid and non-foamed film and sheet which are obtained by extrusion molding a plastic (e.g., cellophane, polyolefin such as polyethylene and polypropylene, nylon, polyester and the like). In addition, foamed film and sheet obtained by extrusion foaming the above-mentioned plastic, nonwoven fabric and woven fabric of plastic fiber, paper, flat board and crape paper of cellulose pulp, and the like may be used as the substrate.

The composition may be combined with a substrate to form, for example, a laminate structure wherein a controlled release composition is applied onto one or both sides of the above-mentioned non-foamed or foamed film or sheet, a sandwich structure or multi-layer structure further including, on said coating layer, a different film, sheet, nonwoven fabric, woven fabric or paper, a structure wherein a fibrous substrate, such as nonwoven fabric and woven fabric of plastic fiber, paper, flat board and crape paper of cellulose pulp, and the like, is coated on the surface, an impregnation structure wherein the composition is entrapped between the fibers of the above-mentioned fibrous substrate or other structure. The controlled release composition contained in the above-mentioned laminate structure, sandwich structure, multi-layer structure or impregnation structure may be a continuous product (non-powdery product) obtained by cooling and solidifying a molten composition. Alternatively, a powder or granules of said composition may be rubbed into a substrate. In the case of the above-mentioned sandwich structure, one film to sandwich the composition may be a gas permeable type film, such as unoriented polypropylene film, and the other film may be a gas barrier type film, such as polyester film, whereby the controlled release composition layer between the films mainly or substantially exerts the function of a volatile compound only on one side thereof, which mode being particularly preferable in the present invention.

Inasmuch as the controlled release composition of the present invention is thermoplastic, it can be processed easily into the above-mentioned various forms. For example, the processing includes pouring the composition of the present invention into a mold while it is still molten immediately after production, or if once cooled to a solid, after melting the solid by heating, or applying same onto the surface of the substrate, or conversely dipping the substrate in a bath of the molten composition. A powdery composition can be obtained by pulverizing the aforesaid plate or block product, or delivering the composition immediately after production while it is still molten, from a nozzle, followed by cooling, or pulverizing as necessary the delivered and cooled product.

By determining the kind of the volatile compound or controlling the amount thereof to be used, the controlled release compositions of the present invention having various release rates of the volatile compound in vapor can be obtained. For example, when the volatile compound is allyl isothiocyanate (hereinafter abbreviated as AIT), the release rate may be made extremely slow to enable long-term sustained or controlled release of the compound to maintain antimicrobial action, freshness retaining action, insecticidal action and the like over an extended period of time, or the rate may be somewhat accelerated to safely preserve a product susceptible to rot in a short time, such as a packed lunch.

The volatile compound is preferably added in an appropriate amount according to the kind of the volatile compound to be used or the object of use. For example, when the volatile compound is AIT and the composition of the present invention is used for prevention of rot of a packed lunch, retaining freshness of fresh food and the like, a small amount of AIT is desirably released rather quickly, in which case the preferable amount is about 0.2 to 20 parts by weight of AIT per 100 parts by weight of rosin. When it is used for insectproof action and fungiproof action in a wardrobe or used as a fungiproof wall paper or insectproof sheet or filter, a small amount of AIT is desirably released in an extremely controlled manner, in which case the preferable amount is about 0.2 to 15 parts by weight of AIT per 100 parts by weight of rosin.

The AIT controlled release composition of the present invention can be used for emission of aroma, antimicrobial effect, antibacterial effect, insecticidal action, insectproof effect, fungicidal action, fungiproof action, freshness retention, antiseptic or preservative effect and the like. For example, it can be used appropriately for foods and various articles in which growth and proliferation of deleterious microorganisms pose problems, since it has bacteriocidal and bacteriostatic actions against aerobic bacteria and anaerobic bacteria, as well as moldcidal, moldstatic and moldproof actions. In addition, it is useful as a preservative effective for freshness retention and prevention of putrefaction and fermentation of foodstuff, as well as a preservative for leather products, books and works of art (particularly antique). Moreover, the composition of the present invention and a controlled release preparation containing said composition can eradicate or avoid harmful insects and is useful as an insectproof agent for building materials, agricultural products and clothings.

The microorganisms to be treated with the antimicrobial agent include, for example, fungi such as mold and yeast, bacteria such as Staphylococcus, *Escherichia coli, Salmonella typhi*, Vibrio and the like, algae and other deleterious microorganisms.

The present invention is described in more detail by way of Examples, which should not be construed as limiting the invention.

EXAMPLE 1

A rosin (1000 g, trademark AA-G, manufactured by Arakawa Chemical Industry Co. Ltd.) and phosphoric ester (100 g, 2-ethylhexyldiphenylphosphate: trademark #41, manufactured by Daihachi Chemical Industry Co., Ltd.) were heated in a 20 l Henschel mixer (manufactured by MITSUI MINING COMPANY, LIMITED) to 85° C. to liquidize same by melting, and a first grade reagent d-limonene (100 g) was cast therein. Impeller was rotated at 500 rpm for 5 min and the mixture was cooled to solidness to give a controlled release composition in the form of block containing limonene.

EXAMPLE 2

In the same manner as in Example 1 with regard to method and conditions, except that 2000 g of rosin (trademark AA-G, manufactured by Arakawa Chemical Industry Co. Ltd.) was used, a controlled release composition in the form of block containing limonene was obtained.

EXAMPLE 3

In the same manner as in Example 1 with regard to method and conditions, except that 500 g of rosin (trademark AA-G, manufactured by Arakawa Chemical Industry Co. Ltd.) was used, a controlled release composition in the form of block containing limonene was obtained.

EXAMPLE 4

A rosin (1000 g, trademark AA-G, manufactured by Arakawa Chemical Industry Co. Ltd.) and phosphoric ester (100 g, 2-ethylhexyldiphenylphosphate: trademark #41, manufactured by Daihachi Chemical Industry Co., Ltd.) were heated in a 20 l Henschel mixer (manufactured by MITSUI MINING COMPANY, LIMITED) to 85° C. to liquidize same by melting, and AIT (100 g) was cast therein. Impeller was rotated at 500 rpm for 5 min and the mixture was cooled to solidness to give a controlled release composition in the form of block containing AIT.

EXAMPLE 5

In the same manner as in Example 4 with regard to method and conditions, except that 2000 g of rosin (trademark AA-G, manufactured by Arakawa Chemical Industry Co. Ltd.) was used, a controlled release composition in the form of block containing AIT was obtained.

EXAMPLE 6

In the same manner as in Example 4 with regard to method and conditions, except that 500 g of rosin (trademark AA-G, manufactured by Arakawa Chemical Industry Co. Ltd.) was used, a controlled release composition in the form of block containing AIT was obtained.

EXAMPLE 7

A rosin (1000 g, trademark AA-G, manufactured by Arakawa Chemical Industry Co. Ltd.) and fatty acid ester (100 g, sorbitan fatty acid ester: trademark L-10(F), manufactured by Kao Corporation) were heated in a 20 l Henschel mixer (manufactured by MITSUI MINING COMPANY, LIMITED) to 85° C. to liquidize same by melting, and a first grade reagent d-limonene (100 g) was cast therein. Impeller was rotated at 500 rpm for 5 min and the mixture was cooled to solidness to give a controlled release composition in the form of block containing limonene.

EXAMPLE 8

In the same manner as in Example 7 with regard to method and conditions, except that 2000 g of rosin (trademark AA-G, manufactured by Arakawa Chemical Industry Co. Ltd.) was used, a controlled release composition in the form of block containing limonene was obtained.

EXAMPLE 9

In the same manner as in Example 7 with regard to method and conditions, except that 500 g of rosin (trademark AA-G, manufactured by Arakawa Chemical Industry Co. Ltd.) was used, a controlled release composition in the form of block containing limonene was obtained.

EXAMPLE 10

A rosin (1000 g, trademark AA-G, manufactured by Arakawa Chemical Industry Co. Ltd.) and fatty acid ester (100 g, sorbitan fatty acid ester: trademark L-10(F), manufactured by Kao Corporation) were heated in a 20 l Henschel mixer (manufactured by MITSUI MINING COMPANY, LIMITED) to 85° C. to liquidize same by melting, and AIT (100 g) was cast therein. Impeller was rotated at 500 rpm for 5 min and the mixture was cooled to solidness to give a controlled release composition in the form of block containing AIT.

EXAMPLE 11

In the same manner as in Example 10 with regard to method and conditions, except that 2000 g of rosin (trademark AA-G, manufactured by Arakawa Chemical Industry Co. Ltd.) was used, a controlled release composition in the form of block containing AIT was obtained.

EXAMPLE 12

In the same manner as in Example 10 with regard to method and conditions, except that 500 g of rosin (trademark AA-G, manufactured by Arakawa Chemical Industry Co. Ltd.) was used, a controlled release composition in the form of block containing AIT was obtained.

EXAMPLES 13–15

Using the methods and conditions of Examples 10 to 12 but without fatty acid ester, controlled release compositions in the form of block respectively containing AIT of Example 13 (amount of rosin 1000 g, rosin:AIT=100:10), Example 14 (amount of rosin 2000 g, rosin:AIT=100:5) and Example 15 (amount of rosin 500 g, rosin:AIT=100:20) were obtained.

EXAMPLES 16–18

According to the method and conditions of Example 10 but without fatty acid ester and using variable amounts of AIT, controlled release compositions in the form of block respectively containing AIT of Example 16 (rosin:AIT=100:1), Example 17 (rosin:AIT=100:50) and Example 18 (rosin:AIT=100:75) were obtained.

EXAMPLE 19

Immediately after mixing in a Henschel mixer, the controlled release composition of Example 4 containing AIT was applied onto a 20 μm thick unoriented polypropylene film, and a 25 μm thick polyester film was coated thereon to give a controlled release preparation having a three-layer structure. The thickness of the controlled release composition layer in the preparation after cooling was 10 μm.

EXAMPLE 20

In the same manner as in Example 19 using the same film, the controlled release composition of Example 5 containing AIT was prepared into a controlled release preparation having a three-layer structure. The thickness of the controlled release composition layer in the preparation after cooling was 10 μm.

EXAMPLE 21

In the same manner as in Example 19 using the same film, the controlled release composition of Example 6 containing AIT was prepared into a controlled release preparation having a three-layer structure. The thickness of the controlled release composition layer in the preparation after cooling was 10 μm.

EXAMPLE 22

A rosin (1000 g, trademark AA-G, manufactured by Arakawa Chemical Industry Co. Ltd.) and phosphoric ester (120 g, 2-ethylhexyldiphenylphosphate: trademark #41, manufactured by Daihachi Chemical Industry Co., Ltd.) were heated in a 20 l Henschel mixer (manufactured by MITSUI MINING COMPANY, LIMITED) to 85° C. to liquidize same by melting, and AIT (60 g) was cast therein. Impeller was rotated at 500 rpm for 5 min. Then, using the film and the method of Example 19, a controlled release preparation having a three-layer structure was obtained. The thickness of the controlled release composition layer in the preparation after cooling was 10 μm.

COMPARATIVE EXAMPLE 1 d-Limonene (1.5 g) cast into a 50 mm φ dish in the thickness of about 3 mm.

COMPARATIVE EXAMPLE 2

A rosin (1500 g, trademark AA-G, manufactured by Arakawa Chemical Industry Co. Ltd.) and phosphoric ester (1 g, 2-ethylhexyldiphenylphosphate: trademark #41, manufactured by Daihachi Chemical Industry Co., Ltd.) were heated in a 20 l Henschel mixer (manufactured by MITSUI MINING COMPANY, LIMITED) to 85° C. to liquidize same by melting, and a first grade reagent d-limonene (1 g) was cast therein. Impeller was rotated at 500 rpm for 5 min. Cooling the mixture to solidness gave a composition in the form of block containing limonene.

COMPARATIVE EXAMPLE 3

In the same manner as in Example 1 with regard to method and conditions, except that 500 g of rosin (trademark AA-G, manufactured by Arakawa Chemical Industry Co. Ltd.), 1000 g of phosphoric ester (2-ethylhexyldiphenylphosphate: trademark #41, manufactured by Daihachi Chemical Industry Co., Ltd.) and 1000 g of d-limonene were used, a composition in the form of a viscous product containing limonene was obtained.

COMPARATIVE EXAMPLE 4

AIT (1.5 g) cast into a 50 mm φ dish in the thickness of about 3 mm.

COMPARATIVE EXAMPLE 5

A rosin (1500 g, trademark AA-G, manufactured by Arakawa Chemical Industry Co. Ltd.) and phosphoric ester (1 g, 2-ethylhexyldiphenylphosphate: trademark #41, manufactured by Daihachi Chemical Industry Co., Ltd.) were heated in a 20 l Henschel mixer (manufactured by MITSUI MINING COMPANY, LIMITED) to 85° C. to liquidize same by melting, and AIT (1 g) was cast therein. Impeller was rotated at 500 rpm for 5 min. Cooling to solidness gave a composition in the form of block containing AIT.

COMPARATIVE EXAMPLE 6

In the same manner as in Example 4 with regard to method and conditions, except that 500 g of rosin (trademark AA-G, manufactured by Arakawa Chemical Industry Co. Ltd.), 1000 g of phosphoric ester (2-ethylhexyldiphenylphosphate:trademark #41, manufactured by Daihachi Chemical Industry Co., Ltd.) and 1000 g of AIT were used, a composition in the form of a viscous product containing limonene was obtained.

COMPARATIVE EXAMPLE 7

AIT (1.5 g) cast into a 50 mm φ dish in the thickness of about 3 mm (same with Comparative Example 1).

COMPARATIVE EXAMPLE 8

A rosin (1500 g, trademark AA-G, manufactured by Arakawa Chemical Industry Co. Ltd.) and fatty acid ester (1 g, sorbitan fatty acid ester: trademark L-10(F), manufactured by Kao Corporation) were heated in a 20 l Henschel mixer (manufactured by MITSUI MINING COMPANY, LIMITED) to 85° C. to liquidize same by melting, and a first grade reagent d-limonene (1 g) was cast therein. Impeller was rotated at 500 rpm for 5 min and the mixture was cooled to solidness to give a composition in the form of block containing limonene.

COMPARATIVE EXAMPLE 9

In the same manner as in Example 7 with regard to method and conditions, except that 500 g of rosin (trademark AA-G, manufactured by Arakawa Chemical Industry Co. Ltd.), 1000 g of fatty acid ester (sorbitan fatty acid ester: trademark L-10(F), manufactured by Kao Corporation) and 1000 g of d-limonene were used, a composition in the form of a viscous product containing limonene was obtained.

COMPARATIVE EXAMPLE 10

AIT (1.5 g) cast into a 50 mm φ dish in the thickness of about 3 mm (same with Comparative Example 4).

COMPARATIVE EXAMPLE 11

A rosin (1500 g, trademark AA-G, manufactured by Arakawa Chemical Industry Co. Ltd.) and 1 g of fatty acid ester (sorbitan fatty acid ester: trademark L-10(F), manufactured by Kao Corporation) were heated in a 20 l Henschel mixer (manufactured by MITSUI MINING COMPANY, LIMITED) to 85° C. to liquidize same by melting, and AIT (1 g) was cast therein. Impeller was rotated at 500 rpm for 5 min and the mixture was cooled to solidness to give a composition in the form of block containing AIT.

COMPARATIVE EXAMPLE 12

In the same manner as in Example 10 with regard to method and conditions, except that 500 g of rosin (trademark AA-G, manufactured by Arakawa Chemical Industry Co. Ltd.), 1000 g of fatty acid ester (sorbitan fatty acid ester: trademark L-10(F), manufactured by Kao Corporation) and 1000 g of AIT were used, a composition in the form of a viscous product containing AIT was obtained.

COMPARATIVE EXAMPLE 13

AIT (1.5 g) cast into a 50 mm φ dish in the thickness of about 3 mm (same with Comparative Examples 4 and 10).

COMPARATIVE EXAMPLE 14

In the same manner as in Example 11 with regard to method and conditions but without fatty acid ester, a composition in the form of block containing AIT was obtained.

COMPARATIVE EXAMPLE 15

In the same manner as in Example 12 with regard to method and conditions but without fatty acid ester, a composition in the form of block containing AIT was obtained.

COMPARATIVE EXAMPLE 16

In the same manner as in Example 22 with regard to method and conditions, except that 1000 g of shellac (PEARL-N811, manufactured by Gifu Shellac Manufactory Co. Ltd.) was used instead of rosin, a three-layer structure preparation including a layer (thickness 10 μm) of composition containing AIT was obtained.

EXPERIMENTAL EXAMPLE 1

Figure 2:
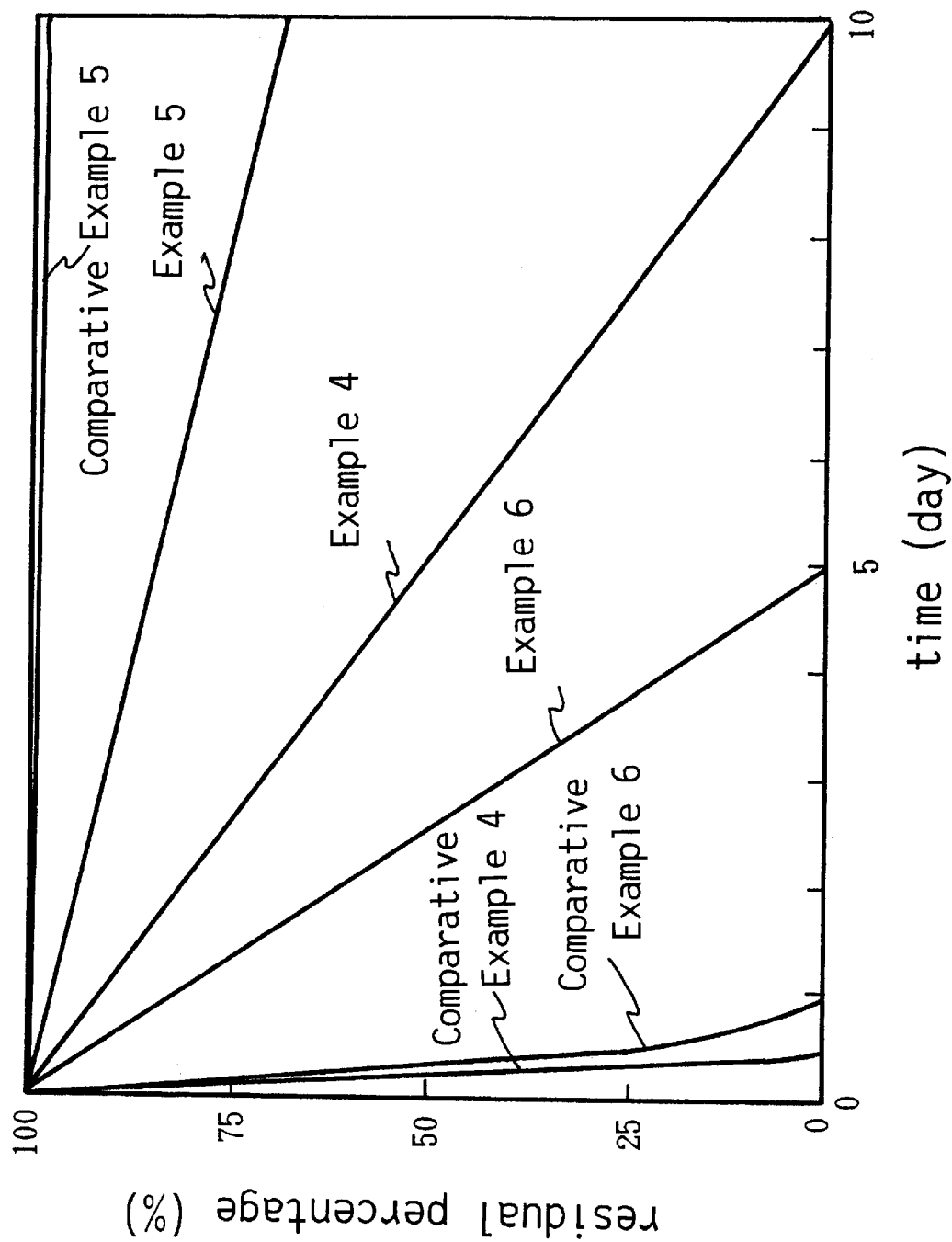
FIG. 2 is a graph showing the residual percentage of contained volatile compounds of Examples 4 to 6 and Comparative Examples 4 to 6 in relation to the time (days) during which the compounds were allowed to stand under isothermal and isohumidity conditions.

The 1 cm×1 cm samples having a thickness of about 3 mm which were obtained in the foregoing Examples 1 to 6 and Comparative Examples 1 to 6 were placed in 50 mm φ dish and left standing in thermo-hygrostat (volume 64 m$^3$, air ventilation rate 60 m$^3$/hr) at 20° C. and relative humidity (RH) of 65%, during which period said 50 mm φ dish was weighed with the lapse of time. The reduced weight was considered to correspond to the volatilized amount of the volatile compound, and volatilization percentage was calculated with time. The results with respect to Examples 1 to 3 and Comparative Examples 1 to 3 are shown in FIG. 1 and the results with respect to Examples 4 to 6 and Comparative Examples 4 to 6 are shown in FIG. 2. In FIGS. 1 and 2, the residual percentage of the volatile substance is shown wherein each percentage in the Figures is an average of 10 samples.

From FIG. 1, the samples of Examples 1 to 3 are known to have been superior in release performance of the volatile compound and markedly superior in the controlled release of d-limonene to the samples of Comparative Examples 1 to 3. Meanwhile, it is known from FIG. 2 that the samples of Examples 4 to 6 were superior in release performance of the volatile compound and noticeably superior in the controlled release of AIT to the samples of Comparative Examples 4 and 6. In Comparative Example 2 wherein d-limonene was used in an excessively small amount and in Comparative Example 5 wherein AIT was used in an excessively small amount, the volatile compound was not substantially volatilized.

EXPERIMENTAL EXAMPLE 2

Figure 3:
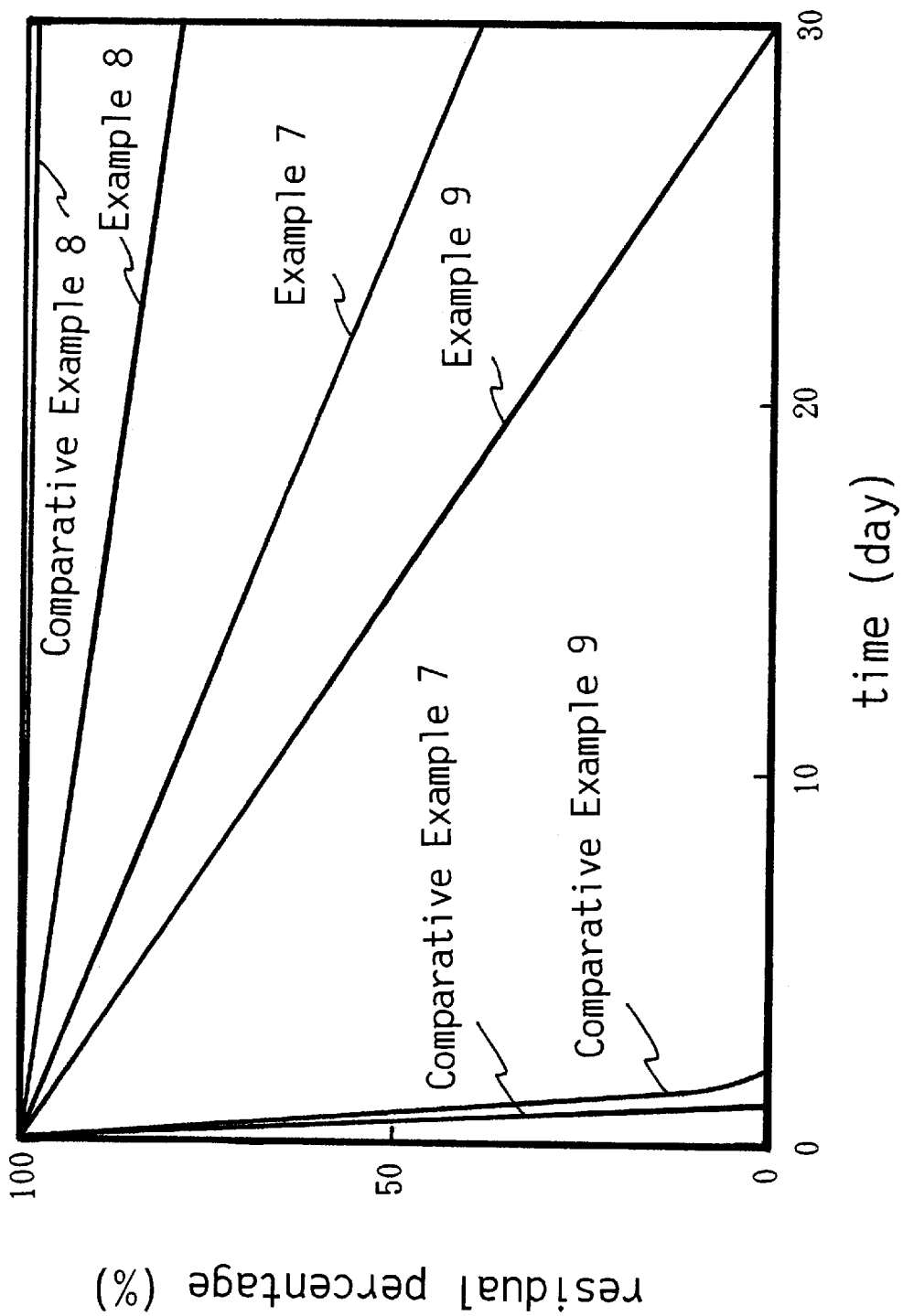
FIG. 3 is a graph showing the residual percentage of contained volatile compounds of Examples 7 to 9 and Comparative Examples 7 to 9 in relation to the time (days) during which the compounds were allowed to stand under isothermal and isohumidity conditions.
Figure 4:
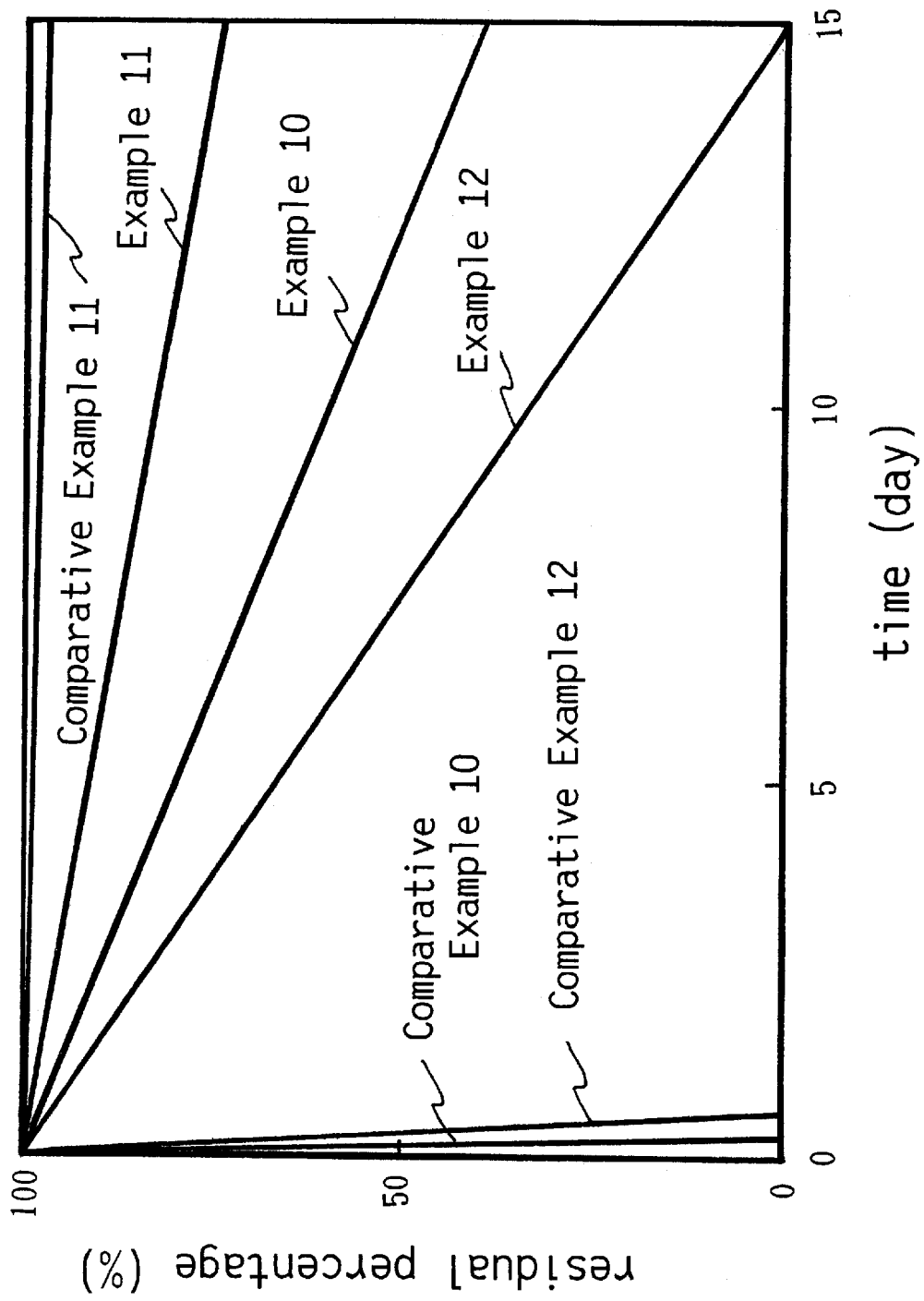
FIG. 4 is a graph showing the residual percentage of contained volatile compounds of Examples 10 to 12 and Comparative Examples 10 to 12 in relation to the time (days) during which the compounds were allowed to stand under isothermal and isohumidity conditions.

The 1 cm×1 cm samples having a thickness of about 3 mm which were obtained in the foregoing Examples 7 to 12 and Comparative Examples 7 to 12 were examined in the same manner as in Experimental Example 1 under the same conditions, for release performance and controlled release. The results with respect to Examples 7 to 9 and Comparative Examples 7 to 9 are shown in FIG. 3 and the results with respect to Examples 10 to 12 and Comparative Examples 10 to 12 are shown in FIG. 4. In FIGS. 3 and 4, the residual percentage of the volatile substance is shown wherein each percentage in the Figures is an average of 10 samples.

From FIG. 3, the samples of Examples 7 to 9 are known to have been superior in release performance of d-limonene and markedly superior in the controlled release of d-limonene to the samples of Comparative Examples 7 and 9. Meanwhile, it is known from FIG. 4 that the samples of Examples 10 to 12 were superior in release performance of AIT and noticeably superior in the controlled release of AIT to the samples of Comparative Examples 10 and 12. In Comparative Example 8 wherein d-limonene was used in an excessively small amount and in Comparative Example 11 wherein AIT was used in an excessively small amount, the volatile compound was not substantially volatilized.

EXPERIMENTAL EXAMPLE 3

The 1 cm×1 cm samples having a thickness of about 3 mm which were obtained in the foregoing Examples 13 to 18 and Comparative Examples 13 to 15 were examined in the same manner as in Experimental Example 1 under the same conditions, for release performance and controlled release. The results are shown in FIG. 5 wherein shown is the residual percentage of the volatile compound in an average of 10 samples.

Figure 5:
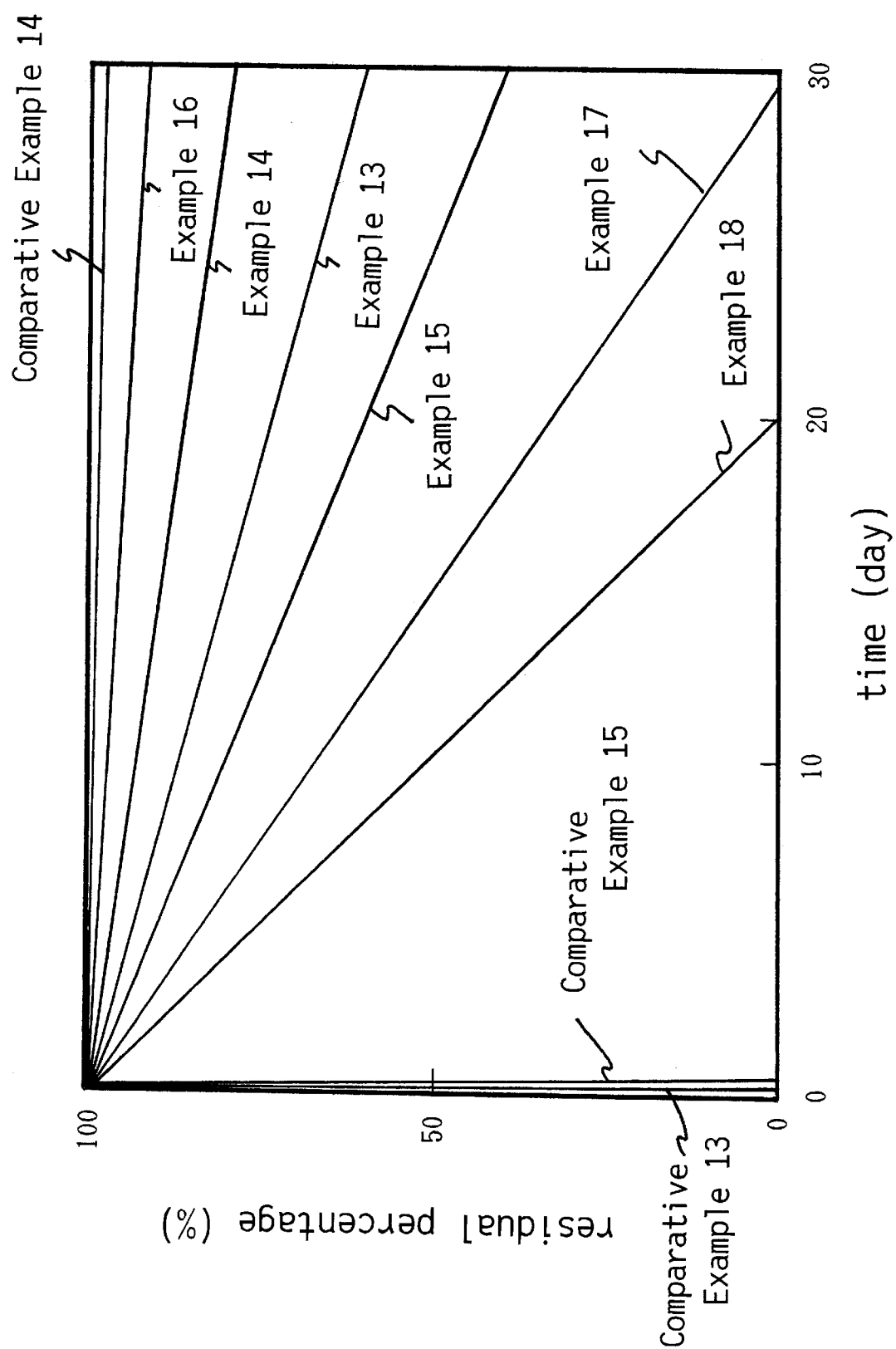
FIG. 5 is a graph showing the residual percentage of contained volatile compounds of Examples 13 to 18 and Comparative Examples 13 to 15 in relation to the time (days) during which the compounds were allowed to stand under isothermal and isohumidity conditions.

From FIG. 5, the samples of Examples 13 to 18 are known to have been superior in release performance of AIT and markedly superior in the controlled release of AIT to the samples of Comparative Examples 13 and 15. In Comparative Example 14 wherein AIT was used in an excessively small amount, the volatile compound was not substantially volatilized.

EXPERIMENTAL EXAMPLE 4

The 20 cm×30 cm samples were cut out from each controlled release preparation of Examples 19 to 22 and left standing in thermo-hygrostat (volume 64 m$^3$, air ventilation rate 60 m$^3$/hr) at 20° C., 65% RH, during which period the samples were weighed with the lapse of time. The reduced weight was considered to correspond to the volatilized amount of the volatile compound, and volatilization percentage was calculated with time (average of three samples). As a result, each preparation of the Examples showed stable controlled release of AIT over about 1.5 to 2 days.

EXPERIMENTAL EXAMPLE 5

The controlled release preparations of Examples 19 to 22 were cut such that each piece contained the total amount of 6 mg of AIT to give samples. In the meantime, a diluted liquid of *Escherichia coli* was coated on the surface of a desoxycholate agar medium in a dish to prepare a test material. The test material was placed in a typical lunch box and each sample was put on the test material, after which the box was lidded. The lunch box was incubated at 25° C. for 24 hours. As a control, a test material without AIT preparation was subjected to the test. After 24 hrs of incubation, no colony was found on the surface of the medium with the sample strips of Examples, whereas red colonies were formed in the control.

EXPERIMENTAL EXAMPLE 6

Figure 6:
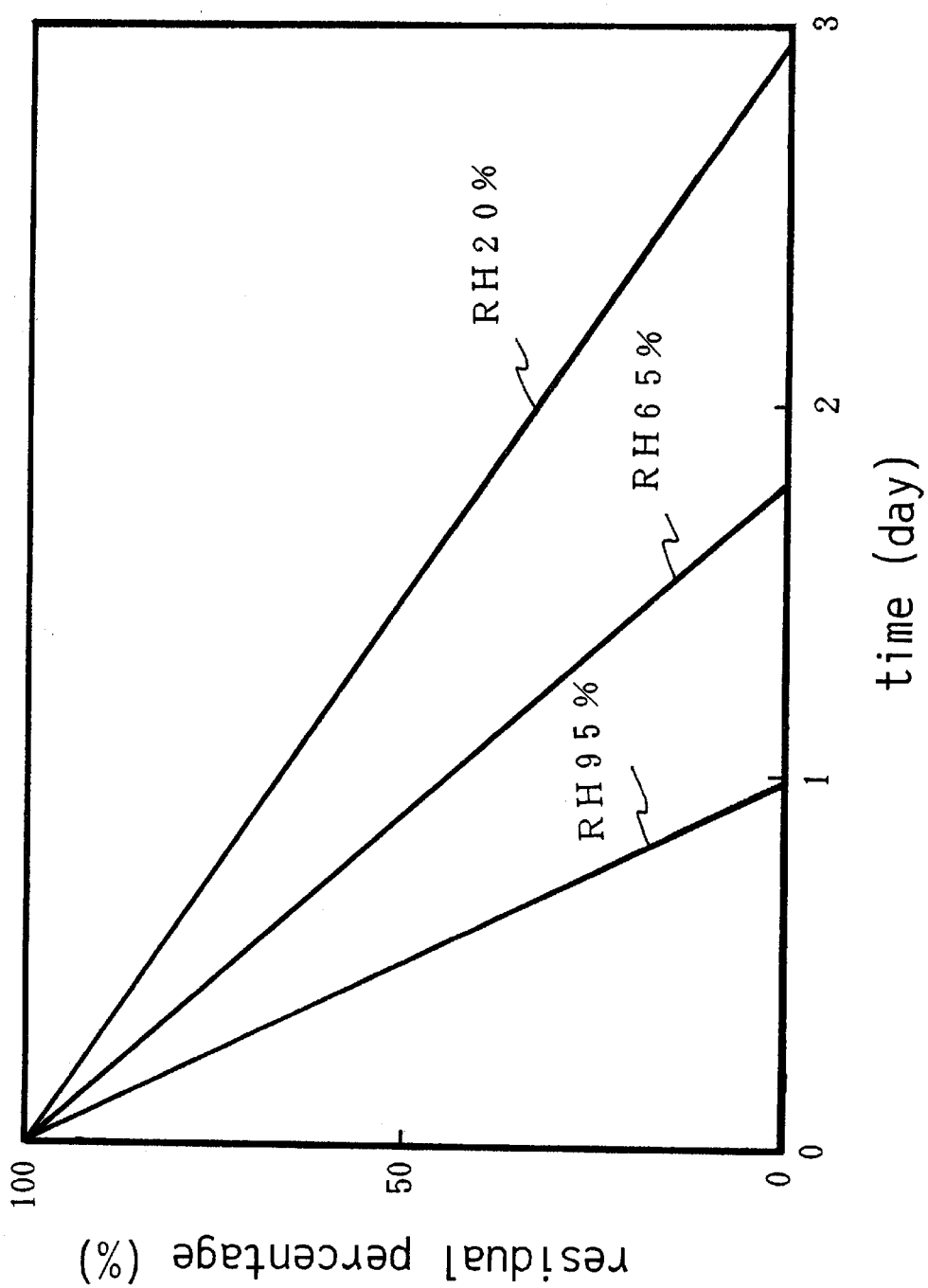
FIG. 6 is a graph showing the residual percentage of contained volatile compound of Example 22 in relation to the time (days) during which the compound was allowed to stand, wherein relative humidity was used as a parameter.
Figure 7:
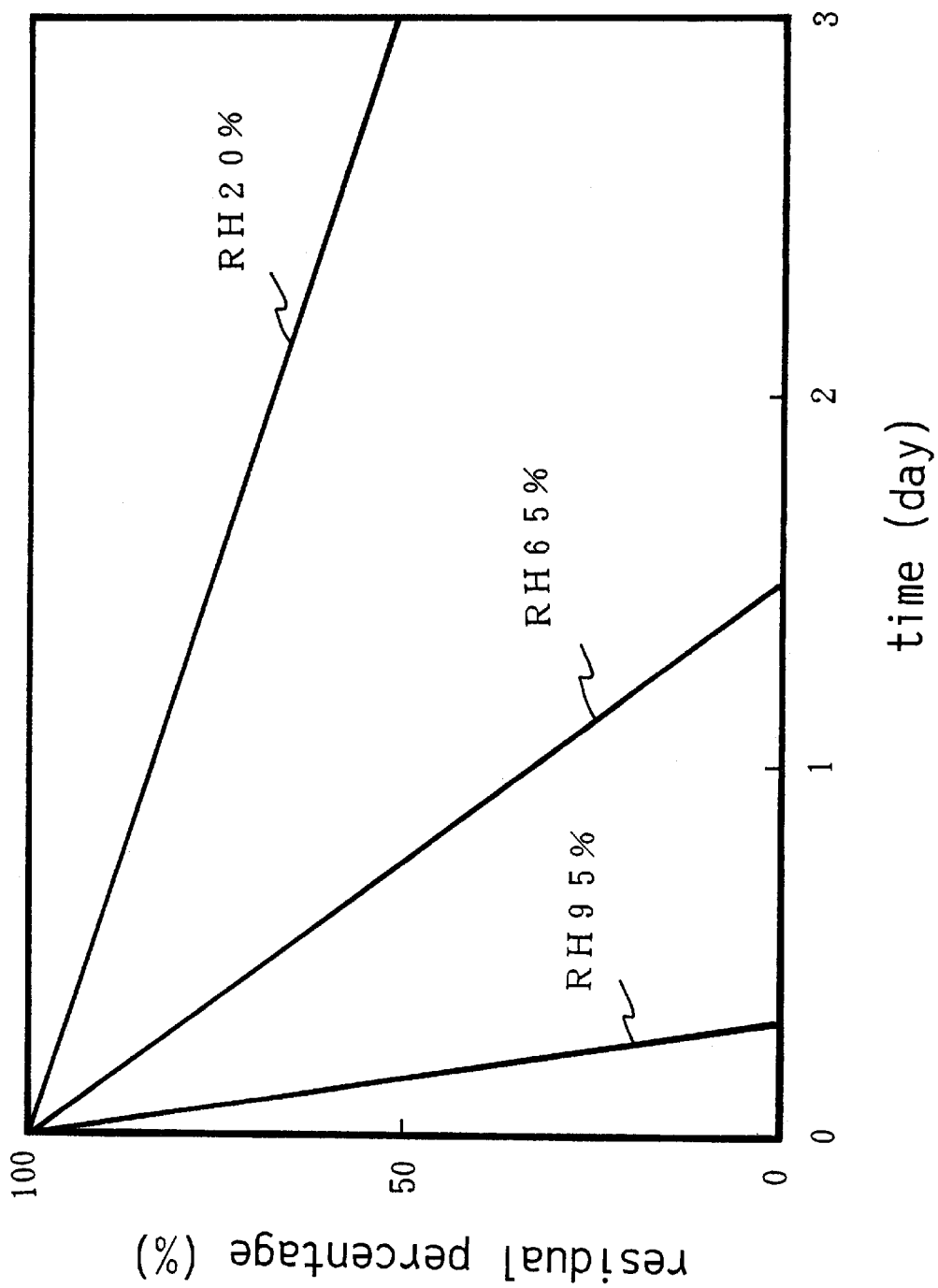
FIG. 7 is a graph showing the residual percentage of contained volatile compound of Comparative Example 16 in relation to the time (days) during which the compound was allowed to stand, wherein relative humidity was used as a parameter.

The 10 cm×10 cm samples were cut out from each controlled release preparation of Example 22 and Comparative Example 16, and used for the evaluation of stability of controlled release against humidity. The samples were left standing in thermo-hygrostat (volume 64 m$^3$, air ventilation rate 60 m$^3$/hr) at 20° C. and RH of 20%, 65% and 95%, during which period the samples were weighed with the lapse of time. The reduced weight was considered to correspond to the volatilized amount of the volatile compound, and volatilization percentage was calculated with time. The results with respect to Example 22 are shown in FIG. 6 and the results with respect to Comparative Example 16 are shown in FIG. 7. In the FIGS. 6 and 7, shown is the residual percentage of the volatile compound in an average of 10 samples.

Comparison of the results in FIGS. 6 and 7 reveal that the composition of Example 22 using rosin as a base material strikingly reduced influence of humidity on the controlled release, as compared to Comparative Example 16 using shellac as the base material.

According to the present invention, a controlled release composition which shows controlled release of a volatile compound, particularly stable controlled release free from the influence of humidity, can be achieved. The controlled release composition of the present invention can contain volatile compound at high yields when a plasticizer is concurrently used, whereby a controlled release composition having a more stable quality can be provided with ease. The controlled release composition of the present invention can be used appropriately for emission of aroma, antimicrobial effect, antibacterial effect, insecticidal action, insectproof effect, fungicidal action, fungiproof action, freshness retention, antiseptic or preservative effect and the like.

This application is based on application No. 8-139301.

What is claimed is:

1. A solid composition for controlling release of a volatile compound, said composition comprising an intimate mixture of a volatile compound and a rosin, wherein the volatile compound is contained in the composition in a proportion of 0.1–100 parts by weight per 100 parts by weight of the rosin, and the total amount of the rosin and the volatile compound forms at least 60 weight % of the entire weight of the composition.

2. The composition of claim 1 wherein said mixture has been prepared by mixing rosin in the melted state with said volatile compound.

3. The composition of claim 1, wherein the volatile compound is contained in a proportion of 0.2 to 30 parts by weight per 100 parts by weight of the rosin.

4. The composition of any one of claims 1, 2 and 3, wherein the volatile compound is allyl isothiocyanate.

5. The composition of claim 4, further comprising a plasticizer.

6. The composition of claim 5, wherein the plasticizer is contained in a proportion of 1 to 25 parts by weight per 100 parts by weight of the rosin.

7. The composition of claim 5 or 6, wherein the plasticizer is at least one kind selected from the group consisting of fatty acid, fatty acid ester, phosphoric ester and wax.

8. The composition of any one of claims 1, 2, 3, 5 and 6, which is in the form of a plate, block, powder, granule or tablet.

9. The composition of any one of claims 1, 2, 3, 5 and 6, which is adhered to one or both sides of a film or sheet substrate.

10. The composition of any one of claims 1, 2, 3, 5 and 6, which is sandwiched between two substrates.

11. The composition of claim 10, wherein the two substrates are an unoriented polypropylene film and a polyester film.

12. The composition of any one of claims 1, 2, 3, 5 and 6, which is entrapped in a fibrous substrate.

* * * * *